(12) United States Patent
Harvey

(10) Patent No.: US 8,483,461 B2
(45) Date of Patent: Jul. 9, 2013

(54) DIAGNOSTIC IMAGING SYSTEM AND METHOD

(75) Inventor: Paul Royston Harvey, Best (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 11 days.

(21) Appl. No.: 13/119,876

(22) PCT Filed: Sep. 21, 2009

(86) PCT No.: PCT/IB2009/054131
§ 371 (c)(1),
(2), (4) Date: Mar. 18, 2011

(87) PCT Pub. No.: WO2010/035208
PCT Pub. Date: Apr. 1, 2010

(65) Prior Publication Data
US 2011/0166440 A1    Jul. 7, 2011

(30) Foreign Application Priority Data
Sep. 26, 2008    (EP) .................................... 08165188

(51) Int. Cl.
*G06K 9/00* (2006.01)

(52) U.S. Cl.
USPC ........... 382/130; 600/409; 600/410; 600/437; 382/132; 382/131

(58) Field of Classification Search
USPC ...... 600/407–429, 437–469, 473–480; 705/2; 382/130–132
See application file for complete search history.

(56) References Cited

U.S. PATENT DOCUMENTS

| | | | | |
|---|---|---|---|---|
| 4,853,946 A * | 8/1989 | Elliott et al. | ...................... | 378/4 |
| RE36,415 E * | 11/1999 | McKenna | ......................... | 378/4 |
| 6,084,939 A * | 7/2000 | Tamura | ......................... | 378/98.2 |
| 6,287,257 B1 * | 9/2001 | Matichuk | ...................... | 600/437 |
| 6,412,980 B1 * | 7/2002 | Lounsberry et al. | ......... | 378/207 |
| 6,481,887 B1 * | 11/2002 | Mirabella | ..................... | 378/198 |
| 6,491,430 B1 * | 12/2002 | Seissler | ........................ | 378/207 |
| 6,501,827 B1 * | 12/2002 | Takasawa | ...................... | 378/116 |
| 6,504,897 B1 * | 1/2003 | Yonekawa | ...................... | 378/63 |
| 6,504,987 B1 * | 1/2003 | Macken et al. | ............... | 385/135 |
| 6,574,518 B1 * | 6/2003 | Lounsberry et al. | ............ | 700/90 |
| 6,614,873 B1 * | 9/2003 | Taylor et al. | .................... | 378/62 |
| 6,691,064 B2 * | 2/2004 | Vroman | ........................ | 702/183 |
| 6,694,367 B1 * | 2/2004 | Miesbauer et al. | ........... | 709/227 |
| 6,806,487 B2 * | 10/2004 | Tamakoshi et al. | ........... | 250/586 |
| 6,912,481 B2 * | 6/2005 | Breunissen et al. | ......... | 702/184 |

(Continued)

OTHER PUBLICATIONS deBeer et al: "A Distributed Computing System for Magnetic Resonance Imaging: Java-Based Processing and Binding of XML"; Computer Methods and Programs in Biomedicine, 2004, vol. 73, pp. 221-231.

*Primary Examiner* — Sanjay Cattungal

(57) ABSTRACT

A diagnostic imaging system including a plurality of scanning apparatuses. Each scanning apparatus including scanning hardware, a data acquisition system connected to the scanning hardware for generating raw image data representative of an object disposed in an imaging region of the scanning apparatus, and a reconstruction unit processing the raw image data for reconstructing an image representation therefrom. Subsets of the raw image data generated by the data acquisition system of one of the scanning apparatuses are distributed via a communication link among the scanning apparatuses for parallel processing by the reconstruction units of the respective scanning apparatuses.

10 Claims, 2 Drawing Sheets

U.S. PATENT DOCUMENTS

| | | | |
|---|---|---|---|
| 6,999,558 B2* | 2/2006 | Okoda | 378/102 |
| 7,574,030 B2* | 8/2009 | Fors et al. | 382/131 |
| 7,677,799 B2* | 3/2010 | Jensen et al. | 378/205 |
| 7,756,736 B2* | 7/2010 | Nakayama et al. | 705/7.12 |
| 7,764,765 B2* | 7/2010 | Ohta et al. | 378/91 |
| 7,778,390 B2* | 8/2010 | Schliermann | 378/115 |
| 7,863,573 B2* | 1/2011 | Aoki | 250/363.03 |
| 7,885,384 B2* | 2/2011 | Mannar et al. | 378/118 |
| 7,907,987 B2* | 3/2011 | Dempsey | 600/411 |
| 7,970,623 B2* | 6/2011 | Miyauchi et al. | 705/2 |
| 8,107,469 B2* | 1/2012 | Jain et al. | 370/389 |
| 2002/0031086 A1* | 3/2002 | Welin | 370/229 |
| 2002/0087359 A1* | 7/2002 | Bocionek | 705/2 |
| 2002/0152395 A1* | 10/2002 | Zhang et al. | 713/200 |
| 2002/0152400 A1* | 10/2002 | Zhang et al. | 713/201 |
| 2002/0161990 A1* | 10/2002 | Zhang et al. | 713/1 |
| 2002/0188652 A1* | 12/2002 | Goldhaber et al. | 709/201 |
| 2002/0198997 A1* | 12/2002 | Linthicum et al. | 709/227 |
| 2003/0156683 A1* | 8/2003 | Adachi | 378/117 |
| 2003/0181804 A1* | 9/2003 | Gagnon et al. | 600/410 |
| 2003/0206609 A1 | 11/2003 | Kling et al. | |
| 2003/0215125 A1* | 11/2003 | Yokoi et al. | 382/131 |
| 2004/0028174 A1* | 2/2004 | Koren | 378/4 |
| 2004/0138920 A1* | 7/2004 | Sawanaga et al. | 705/2 |
| 2004/0138923 A1* | 7/2004 | Routh et al. | 705/2 |
| 2005/0024695 A1* | 2/2005 | Prakash | 358/504 |
| 2005/0080326 A1* | 4/2005 | Mathew | 600/407 |
| 2006/0116567 A1 | 6/2006 | Nilsen et al. | |
| 2006/0184027 A1 | 8/2006 | Watanabe et al. | |
| 2006/0238195 A1 | 10/2006 | Graesslin et al. | |
| 2007/0192408 A1 | 8/2007 | Konig | |

* cited by examiner

DIAGNOSTIC IMAGING SYSTEM AND METHOD

FIELD OF THE INVENTION

The present invention relates to the diagnostic imaging arts. It finds particular application in conjunction with diagnostic imaging systems in which raw diagnostic image data from MRI, CT, or PET scanners are reconstructed into an image representation of an examined object.

Furthermore, the invention relates to a method for diagnostic imaging as well as to a computer program for diagnostic imaging.

BACKGROUND OF THE INVENTION

Today, in the field of diagnostic imaging, diagnostic scanning apparatuses such as MRI, CT, PET or ultrasound scanners are widely used to generate images of the interior of an object. Typically, medical diagnostic scanners comprise suitable scanning hardware for non-invasively examining the interior of the object with radiation, electromagnetic fields, ultrasound, and the like. A data acquisition system (DAS) is used to convert the data received via the scanning hardware into digital signals that can be further processed. Each scanning apparatus has its own host computer that controls the examination and the data acquisition, and each scanning apparatus uses its own reconstruction unit that reconstructs the resultant data to generate human-readable images of interior regions of the object. In modern scanners the reconstruction unit is a separate computer, for example a high-performance personal computer (PC), which is connected to the host computer and to the DAS via an Ethernet connection.

The reconstruction process is typically a multi-threaded application in which multiple reconstruction processes can take place in parallel. The acquired raw image data is first decomposed into subsets that can be processed independently. Each subset is then processed by an independent reconstruction process after which the processed subsets are recombined into clinical image data and sent to a database for storage. It is already known in the art that this architecture lends itself to speed improvements by utilizing a distributed processing approach (see for example US 2006/0116567 A1). Nevertheless, the process of reconstruction is often still very time consuming, and can last for hours after the data is gathered, depending on factors such as the modality, method of reconstruction, the size of the imaging region, resolution, and selected image quality and filtering, among other factors.

Therefore, it is readily appreciated that there is a need for an improved diagnostic imaging system. It is an object of the invention to provide a diagnostic imaging system that minimizes reconstruction time.

SUMMARY OF THE INVENTION

In accordance with the present invention, a diagnostic imaging system is disclosed which comprises a plurality of scanning apparatuses. Each scanning apparatus encompasses scanning hardware, a data acquisition system connected to the scanning hardware for generating raw image data representative of an object disposed in an imaging region of the scanning apparatus, and a reconstruction unit processing the raw image data for reconstructing an image representation therefrom. Provision is made for a communication link that distributes subsets of the raw image data generated by the data acquisition system of one of the scanning apparatuses for parallel processing by the reconstruction units of the scanning apparatuses connected via the communication link.

The invention describes a software and hardware architecture that allows multiple scanning apparatuses, that are connected by a communication link (for example a computer network), to utilize the total available reconstruction resources in order to minimize reconstruction time. Reconstruction tasks from each single scanner installation are distributed amongst all the scanning apparatuses on the network. In this way, idle CPU time on the reconstruction units of one scanner can be used by another scanner operating at a physically different location.

On a larger scale, the pool of reconstruction units can be extended to systems in the world-wide installed base (for example via the Internet). A single scanning apparatus in a hospital can use the reconstruction pool from scanning apparatuses installed at other sites in the world. An efficient use of their data reconstruction capacity is enabled by the approach of the invention.

With the approach of the invention it becomes attractive to transport raw image data from all scanners on the network to a central shared image database such as it is used by a PACS system. The need to store image data locally on each scanning apparatus as well as the need to provide hardware for this purpose is eliminated.

In addition to running the parallel reconstruction processes on a single reconstruction unit supplied with each scanning apparatus as it is known in the art (see above), the invention proposes to enable distribution of the image data subsets and reconstruction processes between the reconstruction hardware of a plurality of scanning apparatuses. On a local scale, a hospital that installs multiple diagnostic scanners (for example MRI, CT, or PET scanners) would benefit from the possibility that each scanner is able to use the reconstruction resources from all other scanners available on the network.

Distribution of the subsets of the raw image data among reconstruction units of remote scanning apparatuses can be managed by the host computer of each scanning apparatus via a high speed Ethernet connection and local area network (LAN). The subsets Processed by the remote reconstruction units can be transferred back either to the same scanning apparatus or to a central image database, i.e. the PACS system. When transferred to the PACS system, the images could be viewed on the console of the scanner used for examination by accessing the PACS database. The images can also be viewed at any location that has access to the PACS system.

Management and configuration of the distributed reconstruction and archiving functionality can be managed by a corresponding communications and configuration process running on the host computer of the scanning apparatus. As an alternative, this functionality can be implemented by a separate reconstruction server connected to the network. The reconstruction server can be used to distribute and coordinate the pending reconstruction jobs and to conduct an effective 'load balancing' for the reconstruction units within the diagnostic imaging system of the invention. The overall reconstruction performance can be further optimized in this way.

The invention not only relates to a diagnostic imaging system but also to a method of diagnostic imaging. According to the invention, the method comprises the following steps:

generating raw image data representative of an object disposed in an imaging region of one of a plurality of scanning apparatuses, each of the scanning apparatuses comprising scanning hardware, a data acquisition system connected to the scanning hardware for generating the raw image data, and a reconstruction unit for processing the raw image data for reconstructing an image representation therefrom;

decomposing the raw image data generated by the data acquisition system into subsets;

distributing the subsets of the raw image data via a communication link among the plurality of scanning apparatuses for parallel processing by the reconstruction units of the respective scanning apparatuses;

recombining the subsets processed by the reconstruction units of the scanning apparatuses into an image representation of the object.

A computer program adapted for carrying out the method of the invention can advantageously be implemented on any common computer hardware, which is presently in clinical use for the control of medical scanning apparatuses. The computer program can be provided on suitable data carriers, such as DVD, CD-ROM or diskette. Alternatively, it can also be downloaded by a user from an Internet server.

BRIEF DESCRIPTION OF THE DRAWINGS

The enclosed drawings disclose preferred embodiments of the present invention. It should be understood, however, that the drawings are designed for the purpose of illustration only and not as a definition of the limits of the invention. In the drawings

DETAILED DESCRIPTION OF THE EMBODIMENTS

Figure 1:
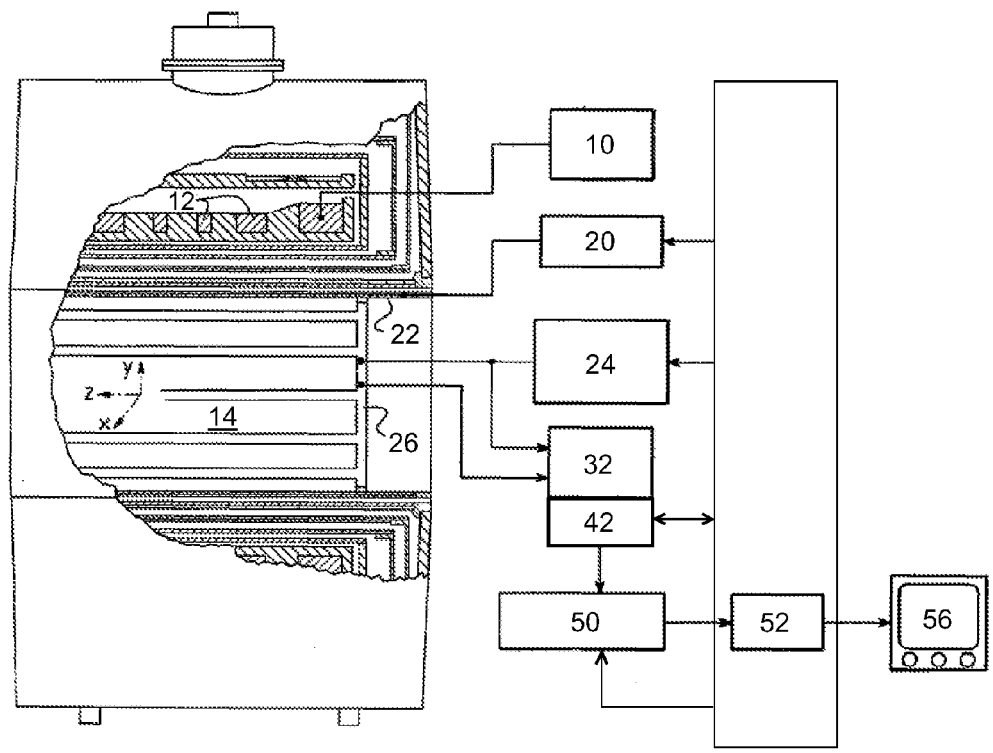
FIG. 1 shows a conventional MR scanner constituting a scanning apparatus within the meaning of the present invention.

With reference to FIG. 1, a main magnetic field control 10 controls superconducting or resistive magnets 12 such that a substantially uniform, temporally constant main magnetic field is created along a z axis through an examination region 14. A magnetic resonance generation and manipulation system applies a series of radio frequency (RF) and magnetic field gradient pulses to invert or excite magnetic spins, induce magnetic resonance, refocus magnetic resonance, manipulate magnetic resonance, spatially and otherwise encode the magnetic resonance, to saturate spin, and the like to generate magnetic resonance imaging and spectroscopy sequences.

More specifically, gradient pulse amplifiers 20 apply current pulses to selected ones or pairs of whole-body gradient coils 22 to create magnetic field gradients along x, y and z-axes of the examination region 14. A digital radio frequency transmitter 24 transmits radio frequency pulses or pulse packets to a whole-body RF coil 26 to transmit RF pulses into the examination region. A typical radio frequency pulse is composed of a packet of immediately contiguous pulse segments of short duration which taken together with each other and any applied gradients achieve a selected magnetic resonance manipulation. The RF pulses are used to saturate, excite resonance, invert magnetization, refocus resonance, or manipulate resonance in selected portions of the examination region. For whole-body applications, the resonance signals are commonly picked up by the whole-body RF coil 26.

For generating images of limited regions of the subject, local coils (not shown) are commonly placed contiguous to the selected region. For example, a receive-only local radio frequency coil can be used to receive resonance signals introduced by body-coil RF transmissions.

The resultant radio frequency signals are picked up by the whole-body RF coil 26 or other specialized RF coils and demodulated by a receiver 32 preferably including a preamplifier (not shown).

A host computer 40 controls the gradient pulse amplifiers 20 and the transmitter 24 to generate any of a plurality of multiple echo sequences such as echo planar imaging, echo volume imaging, gradient and spin echo imaging, fast spin echo imaging, and the like. For the selected sequence, the receiver 32 receives a plurality of data lines in rapid succession following each RF excitation pulse. A data acquisition system (DAS) 42 performs analog-to-digital conversion of the received signals and converts each data line to a digital format suitable for further processing. In modern MM scanners the DAS 42 is a separate computer which is specialized in acquisition of raw image data.

Ultimately, the digital raw image data is reconstructed into an image representation by a reconstruction processor 50 which applies a Fourier transform or other appropriate reconstruction algorithm. The image may represent a planar slice through the patient, an array of parallel planar slices, a three-dimensional volume, or the like. The image is then stored in an image-memory 52 of the host computer 40 where it may be accessed for converting slices, projections, or other portions of the image representation into appropriate format for a display, such as a video monitor 56 which provides a man-readable display of the resultant image.

Figure 2:
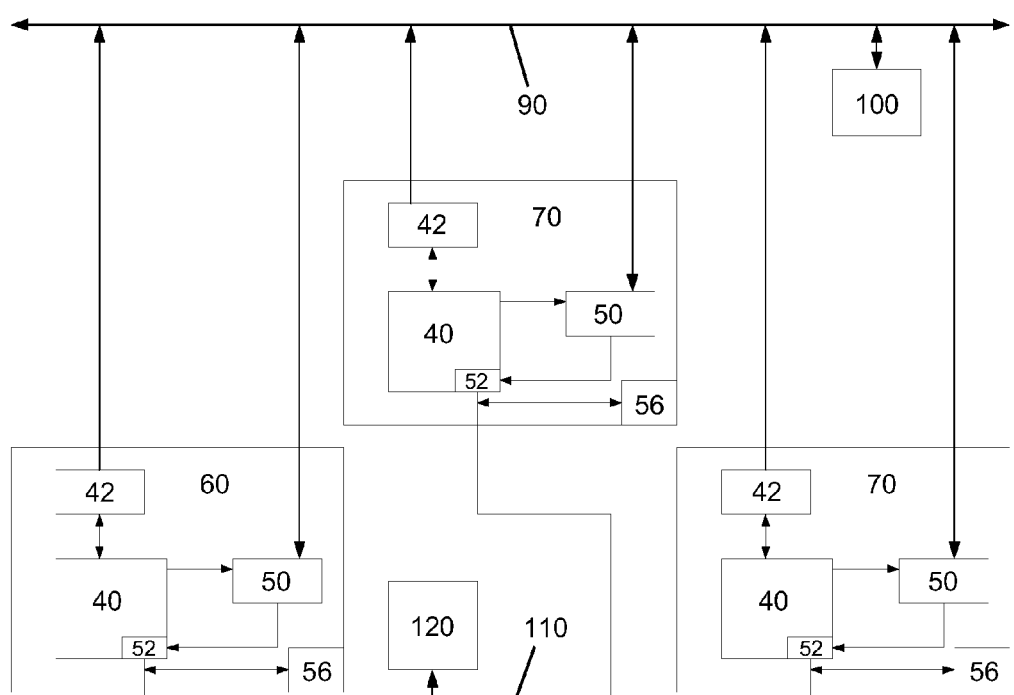
FIG. 2 shows a block diagram of a first embodiment of a diagnostic imaging system according to the invention.

With reference to FIG. 2, a first embodiment of a diagnostic imaging system according to the invention comprises three MR scanners 60, 70, 80 of the type depicted in FIG. 1. The data acquisition systems 42 and the reconstruction units 50 of each MR scanner 60, 70, 80 are connected directly to a dedicated high-speed local area network 90. If, for example, scanner 60 is used for examination of a patient, the host computer 40 of scanner 60 decomposes the raw image data generated by its data acquisition systems 42 into subsets that can be processed independently. A reconstruction server 100, which is also connected to the network 90, manages and coordinates the distribution of the subsets of the raw image data via the network 90 among the scanners 60, 70, 80 for parallel processing by the reconstruction units 50 of the respective scanners 60, 70, 80. Thereafter, the subsets processed by the reconstruction units 50 of the scanners 70 and 80 are transferred via the network 90 back to the reconstruction unit 50 of the scanner 60 where the processed subsets are re-combined into clinical image data. From scanner 60 this image data is sent via a regular hospital network 110, which is separate from the dedicated high-speed network 90, to a hospital PACS database server 120 where the image is stored under the corresponding patient ID. The medical images can be viewed via each video console 56 of the MR scanners 60, 70, 80 by accessing the PACS database server 120.

Figure 3:
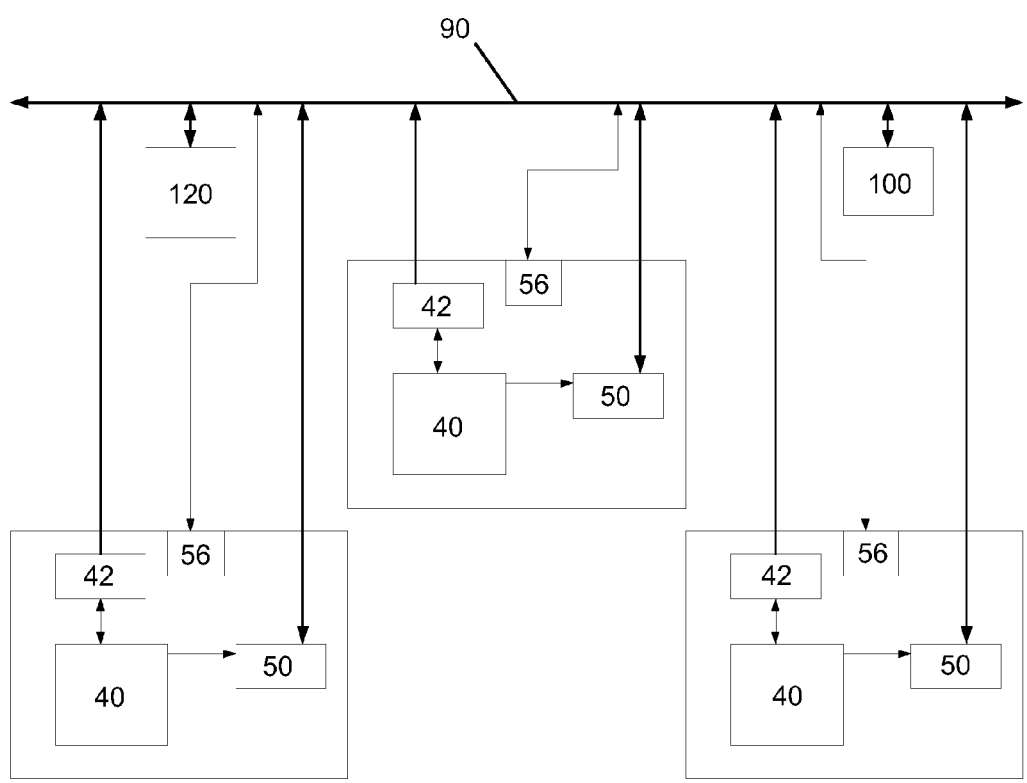
FIG. 3 shows a block diagram of a second embodiment of a diagnostic imaging system according to the invention.

With reference to FIG. 3, only a single network 90 is used for connecting the MR scanners 60, 70, 80 as well as the reconstruction server 100 and the PACS database server 120. The image data subsets processed by the reconstruction units 50 of the scanner 60, 70, 80 are transferred directly via the network 90 to the central PACS database server 120. This version of the invention eliminates the need to store images locally at each scanner 60, 70, 80. The video consoles 56 of the scanners are connected directly to the network 90 for enabling them to access the image data stored in the PACS database 120.

The invention claimed is:

1. A diagnostic imaging system comprising:
a network;

a plurality of scanners connected to the network, each comprising imaging region, an acquisition system for generating raw images representative of an object disposed in the imaging region and a reconstruction unit for reconstructing an image representation from the raw images; and a reconstruction server connected to the network for distributing subsets of the raw images from the data acquisition systems of any of the plurality of scanners to the reconstruction units of any of the plurality of scanners for parallel processing of images wherein each of the plurality of scanner's further comprises a host computer for controlling the acquisition system and the reconstruction unit, and wherein the host computer of each of the plurality of scanners is arranged to perform at least one of: decomposing the raw image generated by the acquisition system into subsets; sending at least one of the subsets via the network to another of the plurality of scanners; recombining the subsets processed in parallel by the reconstruction unit into an image representation of the object.

2. The diagnostic imaging system of claim 1, further comprising a data base connected to the network, wherein the reconstruction server transfers subsets of processed images to one of the plurality of scanners and the data base.

3. The diagnostic imaging system of claim 1, wherein the reconstruction server coordinates the distribution of the subsets of the raw image among available reconstruction units of the plurality of scanners.

4. The diagnostic imaging system of claim 1, wherein the network is the internet.

5. The diagnostic imaging system of claim 1, wherein the plurality of scanners is selected from MRI scanners, CT scanners, PET scanners or ultrasound scanners.

6. A method of diagnostic imaging, the method comprising acts of:
providing a system having a network for connecting a reconstruction server and a plurality of scanners, each including an acquisition system and a reconstruction unit; the acquisition system of each of the plurality of scanners generating raw images representative of an object disposed in an imaging region of that scanner;
the reconstruction unit of each of the plurality of scanners processing the raw image for reconstructing an image representation from the raw images;
decomposing the raw images generated by the acquisition system into subsets;
the reconstruction server distributing the subsets of the raw images from the data acquisition systems of any of to the reconstruction units of any of the plurality of scanners for parallel processing by the reconstruction units of the plurality of scanners;
recombining the subsets processed by the reconstruction units of the plurality of scanners into an image representation of the object.

7. The method of claim 6, wherein the processed subsets are transferred via the network to one of the plurality of scanners or to a data base.

8. The method of claim 6, wherein the distribution of the subsets of the raw images among the available reconstruction units of the plurality of scanners is coordinated by the reconstruction server.

9. A computer program stored on a non-transitory computer readable medium having computer executable instructions for performing a method of diagnostic imaging comprising acts of;
on a system having a network connecting a reconstruction server a plurality of scanners, each including an acquisition system and a reconstruction unit;
the acquisition system of each of the plurality of scanners generating raw images representative of an object disposed in an imaging region of that scanner; and
the reconstruction unit of each of the plurality of scanners processing the raw image for reconstructing an image representation from the raw images;
decomposing the raw images generated by the acquisition system into subsets;
the reconstruction server distributing the subsets of the raw images from the data acquisition systems of any of the reconstruction units to any of the plurality of scanners for parallel processing by reconstruction units of the plurality of scanners;
recombining the subsets processed by the reconstruction unit into an image representation of the object.

10. The computer program of claim 9, further comprising an act of transferring the processed subsets to one of the plurality of scanners or to a data base.

* * * * *